US012797505B2

(12) United States Patent
Greene

(10) Patent No.: US 12,797,505 B2
(45) Date of Patent: Nov. 17, 2026

(54) AIR MOVING SANITATION DEVICE

(71) Applicant: Ralph Gregory Greene, Dalton, GA (US)

(72) Inventor: Ralph Gregory Greene, Dalton, GA (US)

( * ) Notice: Subject to any disclaimer, the term of this patent is extended or adjusted under 35 U.S.C. 154(b) by 237 days.

(21) Appl. No.: 18/889,953

(22) Filed: Sep. 19, 2024

(65) Prior Publication Data

US 2025/0090715 A1 Mar. 20, 2025

Related U.S. Application Data

(60) Provisional application No. 63/539,335, filed on Sep. 20, 2023.

(51) Int. Cl.
*A61L 9/20* (2006.01)
*F04D 25/08* (2006.01)
*F04D 29/32* (2006.01)

(52) U.S. Cl.
CPC ................ *A61L 9/20* (2013.01); *F04D 25/08* (2013.01); *F04D 29/325* (2013.01); *A61L 2209/111* (2013.01); *A61L 2209/12* (2013.01)

(58) Field of Classification Search
CPC .. A61L 9/20; A61L 2209/12; A61L 2209/111; F04D 25/08; F04D 25/325
See application file for complete search history.

(56) References Cited

U.S. PATENT DOCUMENTS

| | | | |
|---|---|---|---|
| 11,400,177 B2 | 8/2022 | Wald et al. | |
| 11,433,154 B2 | 9/2022 | Wald et al. | |
| 11,674,521 B2 | 6/2023 | Rhoades et al. | |
| 11,696,970 B2 | 7/2023 | Wald et al. | |
| 2009/0129974 A1 | 5/2009 | McEllen | |
| 2016/0245298 A1* | 8/2016 | Ohtaguro | F04D 29/281 |
| 2021/0353820 A1 | 11/2021 | Lesser | |
| 2023/0047172 A1 | 2/2023 | McKinzie et al. | |

* cited by examiner

*Primary Examiner* — Sean Luck
(74) *Attorney, Agent, or Firm* — PATENTFILE, LLC; Bradley C. Fach; Steven R. Kick

(57) ABSTRACT

An air moving sanitation device may include a plurality of fan blades 11 that may rotate in a horizontal blade plane. An ultraviolet (UV) light emitting assembly may have one or more UV light emitting elements that are configured to emit UV radiation. A plurality of baffle plates may be coupled to the UV light emitting assembly which may limit the UV radiation emitted by the UV light emitting elements from exceeding above an upper horizontal UV light plane and from exceeding below a lower horizontal UV light plane. A tilt sensor may be configured to detect when the device has been tilted out of vertical, and when the tilt sensor detects that the device has been tilted out of vertical to exceed a tilt threshold, the motion of the fan blades becomes deactivated and/or the one or more UV light emitting elements becomes deactivated.

20 Claims, 11 Drawing Sheets

AIR MOVING SANITATION DEVICE

CROSS REFERENCE TO RELATED APPLICATIONS

This application claims priority to and the benefit of the filing date of U.S. Provisional Application No. 63/539,335, filed on Sep. 20, 2023, entitled "Ceiling Fan UV-C Upper Air Treatment device", which is hereby incorporated by reference in its entirety.

FIELD OF THE INVENTION

This patent specification relates to the field of air treatment and purification devices. More specifically, this patent specification relates to a device configured for the sanitation and purification of air supplied to human living or working spaces via sterilization using UV light.

BACKGROUND

Air sanitation is important for protecting public health, maintaining clean and hygienic environments, improving respiratory health, enhancing comfort and productivity, and addressing environmental concerns. Airborne pathogens such as viruses, bacteria, and fungi can spread illnesses such as the flu, colds, and respiratory infections. Sanitizing the air helps to reduce the concentration of these pathogens, lowering the risk of disease transmission, particularly in crowded or enclosed spaces. Sanitizing the air can also benefit individuals with respiratory conditions such as asthma, allergies, and chronic obstructive pulmonary disease (COPD). By reducing airborne allergens, pollutants, and irritants, air sanitation can help alleviate symptoms and improve respiratory health. Sanitizing the air is essential for maintaining clean and hygienic environments, particularly in healthcare facilities, laboratories, food processing plants, and other settings where contamination control is critical. It helps to prevent the spread of harmful microorganisms and maintain sterile conditions. Air sanitation can help eliminate unpleasant odors caused by organic matter, mold, mildew, smoke, or other sources. By neutralizing odor-causing compounds, sanitized air creates a more pleasant and comfortable indoor environment. Furthermore, clean, sanitized air can contribute to improved productivity, concentration, and comfort in indoor spaces. It may help occupants feel more alert, energized, and focused, leading to a more pleasant and productive work or living environment.

In the past several years, the need for air sanitization and air treatment in work and public spaces has become very urgent with the Covid-19 Virus outbreak but it is also important for protection against other airborne infectious viruses, bacteria's and molds.

There are various types of Air Treatment devices such as HEPA Filtration and UV-C (Ultraviolet Light) that are used to inactivate or trap airborne infectious bacteria, viruses, and molds.

There are generally 2 types of UV-C air treatment devices, one is a "upper air device" which shines UV-C light into the upper part of a room and has baffles to help keep the UV-C light which can be harmful to eyes, skin and some materials from going into occupied parts of the room below a set height for example 7 feet. This type of UV-C air treatment device is simple in design and shines UV-C light externally from the device into an upper part of a room and does not utilize fans to move air through the device or around the room so a separate air moving device or method may be required to enable air movement.

Another type of UV-C air treatment device is an "enclosed" UV-C air treatment device which typically has a fan or fans to pull into a housing enclosure or move air to run the air past the UV-C lamp to treat the air with ultraviolet-C light and then sends the air out of the housing enclosure through a vent or outlet. This type of device generally does not have UV-C Light radiating outside the device and has less risk of exposure for people and materials, however it has a reduced air flow and higher energy requirement.

Therefore, a need exists for novel air treatment and purification devices. A further need exists for novel devices configured for the sanitation and purification of air supplied to human living or working spaces and which are able to remove airborne pathogens, reduce airborne allergens, pollutants, and irritants to help alleviate symptoms of respiratory conditions, reduce disease transmission, and improve respiratory health.

BRIEF SUMMARY OF THE INVENTION

An air moving sanitation device is provided. The device is configured to move air through ultraviolet radiation for sanitization purposes while preventing the ultraviolet radiation from contacting a ceiling and any fixtures, such as sprinkler head covers, above the device, and preventing the ultraviolet radiation from contacting or being observed by individuals that are below the device and that are in the same room or area as the device.

In some embodiments, the device may include: a plurality of fan blades that may be coupled to a motor hub, the plurality of fan blades configured to rotate in a horizontal blade plane; a mounting plate; an ultraviolet (UV) light emitting assembly that may be coupled to the mounting plate and to the motor hub, the UV light emitting assembly positioned between the motor hub and the mounting plate, and the UV light emitting assembly having a UV light emitting element that is configured to emit UV radiation when activated and to stop emitting UV radiation when deactivated; a top baffle plate and a bottom baffle plate that may be coupled to the UV light emitting assembly, in which the top baffle plate may be coupled to the UV light emitting assembly so that the top baffle plate may be relatively closer to the mounting plate than the bottom baffle plate, in which the top baffle plate includes a lower plate surface and the bottom baffle plate includes an upper plate surface, in which the lower plate surface limits the UV radiation emitted by the UV light emitting element from exceeding above an upper horizontal UV light plane, the upper horizontal UV light plane below the mounting plate, and in which the upper plate surface limits the UV radiation emitted by the UV light emitting element from exceeding below a lower horizontal UV light plane, the lower horizontal UV light plane above the horizontal blade plane; and a tilt sensor that may be configured to detect a tilt of the device out of vertical, in which one of rotation of the fan blades and the UV light emitting element is deactivated once the tilt sensor detects that the tilt of the device out of vertical exceeds a tilt threshold In further embodiments, the device may include a plurality of fan blades coupled to a motor hub, the plurality of fan blades configured to rotate in a horizontal blade plane, and a mounting plate. An ultraviolet (UV) light emitting assembly may be coupled to the mounting plate and to the motor hub, the UV light emitting assembly may be positioned between the motor hub and the mounting plate, and the UV light emitting assembly having a UV light emitting element that is configured to emit UV radiation when activated and to stop emitting UV radiation when deactivated. A top baffle plate and a bottom baffle plate may be coupled to the UV light emitting assembly. The top baffle plate may be coupled to the UV light emitting assembly so that the top baffle plate is relatively closer to the mounting plate than the bottom baffle plate. The top baffle plate may include a lower plate surface and the bottom baffle plate may include an upper plate surface. The lower plate surface may limit the UV radiation emitted by the UV light emitting element from exceeding above an upper horizontal UV light plane, the upper horizontal UV light plane below the mounting plate, and the upper plate surface may limit the UV radiation emitted by the UV light emitting element from exceeding below a lower horizontal UV light plane, the lower horizontal UV light plane above the horizontal blade plane. A shroud may surround the UV light emitting element. The shroud may extend above the upper horizontal UV light plane, and the shroud may extend below the lower horizontal UV light plane. Preferably, the shroud does not extend into the horizontal blade plane so that the fan blades are external to the shroud. Air is sanitized by the device by being exposed to UV radiation emitted by the UV light emitting element as it passes between the UV Light emitting element and the shroud, and the shroud may substantially block the UV radiation emitted by the UV light emitting element from passing through the shroud or into an environment outside of the shroud.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Figure 1:
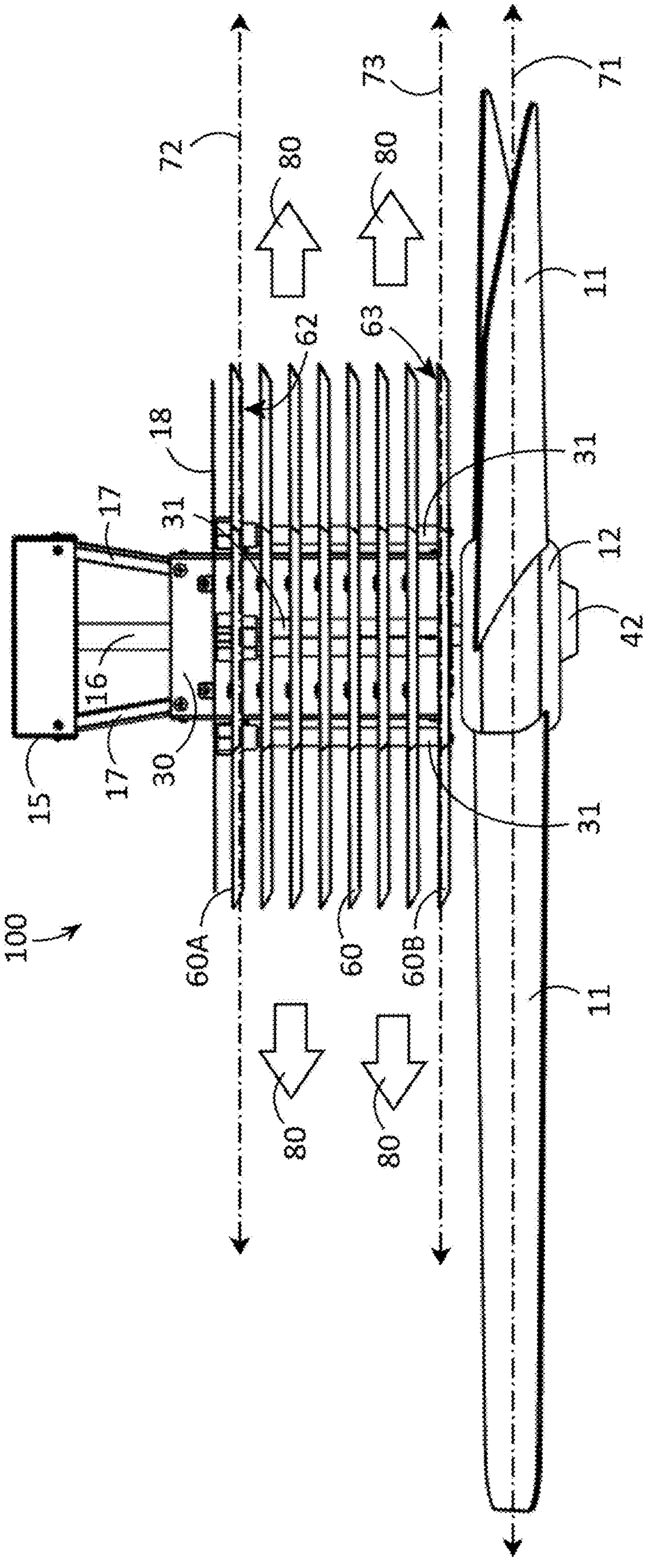
FIG. 1—depicts a side elevation view of an example of an air moving sanitation device according to various embodiments described herein.

For purposes of description herein, the terms "upper," "lower," "left," "right," "rear," "front," "side," "vertical," "horizontal," and derivatives thereof shall relate to the invention as oriented in FIG. 1. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Although the terms "first," "second," etc. are used herein to describe various elements, these elements should not be limited by these terms. These terms are only used to distinguish one element from another element. For example, the first element may be designated as the second element, and the second element may be likewise designated as the first element without departing from the scope of the invention.

As used in this application, the term "about" or "approximately" refers to a range of values within plus or minus 20% of the specified number. Additionally, as used in this application, the term “substantially” means that the actual value is within about 10% of the actual desired value, more preferably within about 5% of the actual desired value and even more preferably within about 1% of the actual desired value of any variable, element or limit set forth herein.

A new air moving sanitation device is discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

The present invention will now be described by example and through referencing the appended figures representing preferred and alternative embodiments. FIG. 1 illustrates an example of an air moving sanitation device (“the device”) 100 according to various embodiments. In some embodiments, the device 100 may comprise a plurality of fan blades 11 that may be coupled to a motor hub 12, and the plurality of fan blades 11 may be configured to rotate in a horizontal blade plane 71 thereby moving air around and through the device 100. An ultraviolet (UV) light emitting assembly 30 may be coupled to a mounting plate 13 and to the motor hub 12. The UV light emitting assembly 30 may be positioned between the motor hub 12 and the mounting plate 13, and the UV light emitting assembly 30 may have one or more UV light emitting elements 31 that are configured to emit UV radiation 80. The device 100 may include a plurality of baffle plates 60 that may be coupled to the UV light emitting assembly 30, and the baffle plates 60 limit the UV radiation 80 emitted by the UV light emitting elements 31 from exceeding above an upper horizontal UV light plane 72 and from exceeding below a lower horizontal UV light plane 73, in which the upper horizontal UV light plane 72 and the lower horizontal UV light plane 73 are each above the horizontal blade plane 71. A tilt sensor 41 may be configured to detect when the device 100 has been tilted out of vertical, and when the tilt sensor 41 detects that the device 100 has been tilted out of vertical to exceed a tilt threshold, the motion of the fan blades becomes deactivated (e.g., stops rotating) and/or the one or more UV light emitting elements 31 becomes deactivated (e.g., stops emitting UV radiation 80).

The device 100 may comprise a mounting plate 13 which may be used to couple the device 100 to a ceiling or other structure that is above the location that the device is to be positioned in. A mounting plate 13 may comprise a horizontal plate of metal or other substantially rigid material that may have one or more apertures for receiving screws or other fasteners that may be used to couple the device 100 to a ceiling and/or to an object or structure that is coupled to a ceiling. One or more vertical walls 14 may be coupled to the mounting plate 13 to form a ceiling mounting box 15. The mounting plate 13 may be coupled to a junction box or ceiling mounting box, as is commonly used in ceiling fan mounting, via a T-grid mounting bracket, as is commonly used in ceiling fan mounting, or the mounting plate 13 may be coupled to a hard or sturdy ceiling as desired. The ceiling height in a room should allow for a mounting height of the device 100 so that the fan blades 11 are above the heads of occupants and generally at heights greater than 7 feet.

Figure 2:
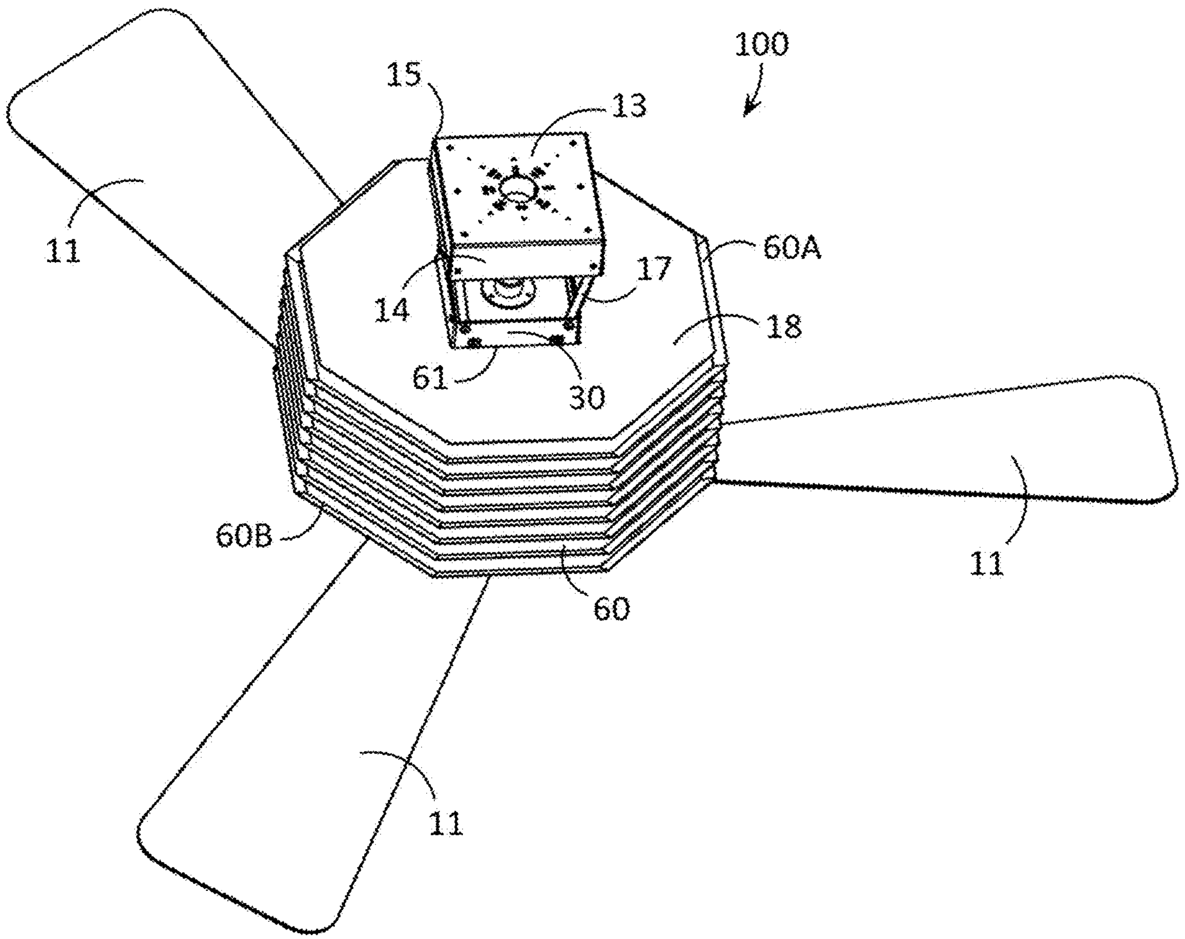
FIG. 2—illustrates a top perspective view of an example of an air moving sanitation device according to various embodiments described herein.

In some embodiments, the device 100 may include an optional downrod 16 and/or one or more optional support arms 17 which may be used to couple the mounting plate 13 (optionally of a ceiling mounting box 15) to the UV light emitting assembly 30. A downrod 16 may comprise an extension pipe, or the like, that may be substantially rigid and suitable for supporting and connecting the UV light emitting assembly 30, fan blades 11, motor hub 12, and baffle plates 60, to the mounting hardware e.g., mounting plate 13, attached to the ceiling. Support arms 17 likewise may be substantially rigid and suitable for supporting and connecting the UV light emitting assembly 30, fan blades 11, motor hub 12, and baffle plates 60, to the mounting hardware e.g., mounting plate 13, attached to the ceiling. For example, a support arm 17 may comprise metal angles, rods or wire cables, etc. The mounting height of the device 100 from the ceiling may be adjusted by changing the length of the downrod 16 in the center and the support arms 17. Preferably, the device 100 may comprise a dust shield 18 which may block dust from settling on the baffle plates and/or which may block UV radiation 80 from traveling above the UV light emitting assembly 30. A dust shield may be configured in any shape or size, such as by being substantially planar in shape as perhaps best shown in FIGS. 1-3.

The device 100 may include a motor hub 12 to which the fan blades 11 may be movably coupled. A motor hub 12 may comprise a housing that may preferably conceal an electric motor 45 that may be configured to rotate the fan blades 11. The motor hub 12 may be coupled to the UV light emitting assembly 30 so that the motor hub 12 may be positioned below the UV light emitting assembly 30. In preferred embodiments, the motor hub 12 may be stationarily coupled to the UV light emitting assembly 30 so that the motor hub 12 does not rotate with the plurality of fan blades 11. In this manner, the motor hub 12 and the motor 45 contained therein may remain stationary when the fan blades 11 are rotating. The motor hub 12 may comprise an electric motor 45 which may be configured to rotate the fan blades 11 in a horizontal blade plane 71. Preferably, the horizontal blade plane 71 may be substantially parallel to a ceiling or other structure that the device 100 may be coupled to.

A motor 45 may comprise any type of electric motor, such as a brushed DC motor, brushless DC motor, switched reluctance motor, universal motor, AC polyphase squirrel-cage or wound-rotor induction motor, AC SCIM split-phase capacitor-start motor, AC SCIM split-phase capacitor-run motor, AC SCIM split-phase auxiliary start winding motor, AC induction shaded-pole motor, wound-rotor synchronous motor, hysteresis motor, synchronous reluctance motor, pancake or axial rotor motor, stepper motor, or any other type of motor.

In preferred embodiments, the device may comprise one or more, such as a plurality, of fan blades 11 which may be rotated in a horizontal blade plane 71 via a motor 45 to move air around the device 100 and in the area that the fan is located in. Fan blades 11 may comprise any type of fan blades that may be suitable for moving air in a space, such as: straight fan blades, these blades have a uniform width and are aligned straight across the fan; curved fan blades, these blades have a curved shape, which helps to increase airflow and reduce noise; sickle fan blades, these blades have a unique shape that resembles a sickle, which helps to improve airflow and reduce turbulence; swept fan blades, these blades have a curved design that sweeps back from the hub, which helps to increase airflow and reduce noise; delta fan blades, these blades have a triangular shape, which helps to improve airflow and reduce noise, and propeller fan blades: these blades have a flat design with a twist, similar to a propeller on an airplane, which helps to generate a powerful airflow.

The device 100 may comprise one or more ultraviolet (UV) light emitting assemblies 30 that may be coupled to a mounting plate 13 and to the motor hub 12. A UV light emitting assembly 30 may have one or more UV light emitting elements 31 that are configured to emit UV radiation 80. Generally, a UV light emitting assembly 30 may comprise a structure to which one or more UV light emitting elements 31 may be coupled. A UV light emitting assembly 30 may comprise one or more sockets or other electrical couplers which one or more UV light emitting elements 31 may be coupled and may be supplied power. In preferred embodiments, a UV light emitting assembly 30 may be positioned between the motor hub 12 and the mounting plate 13. In further preferred embodiments, one or more, such as all UV light emitting elements 31 may be coupled to a UV light emitting assembly 30 so that the UV light emitting elements 31 may be positioned between the motor hub 12 and the mounting plate 13.

Figure 6:
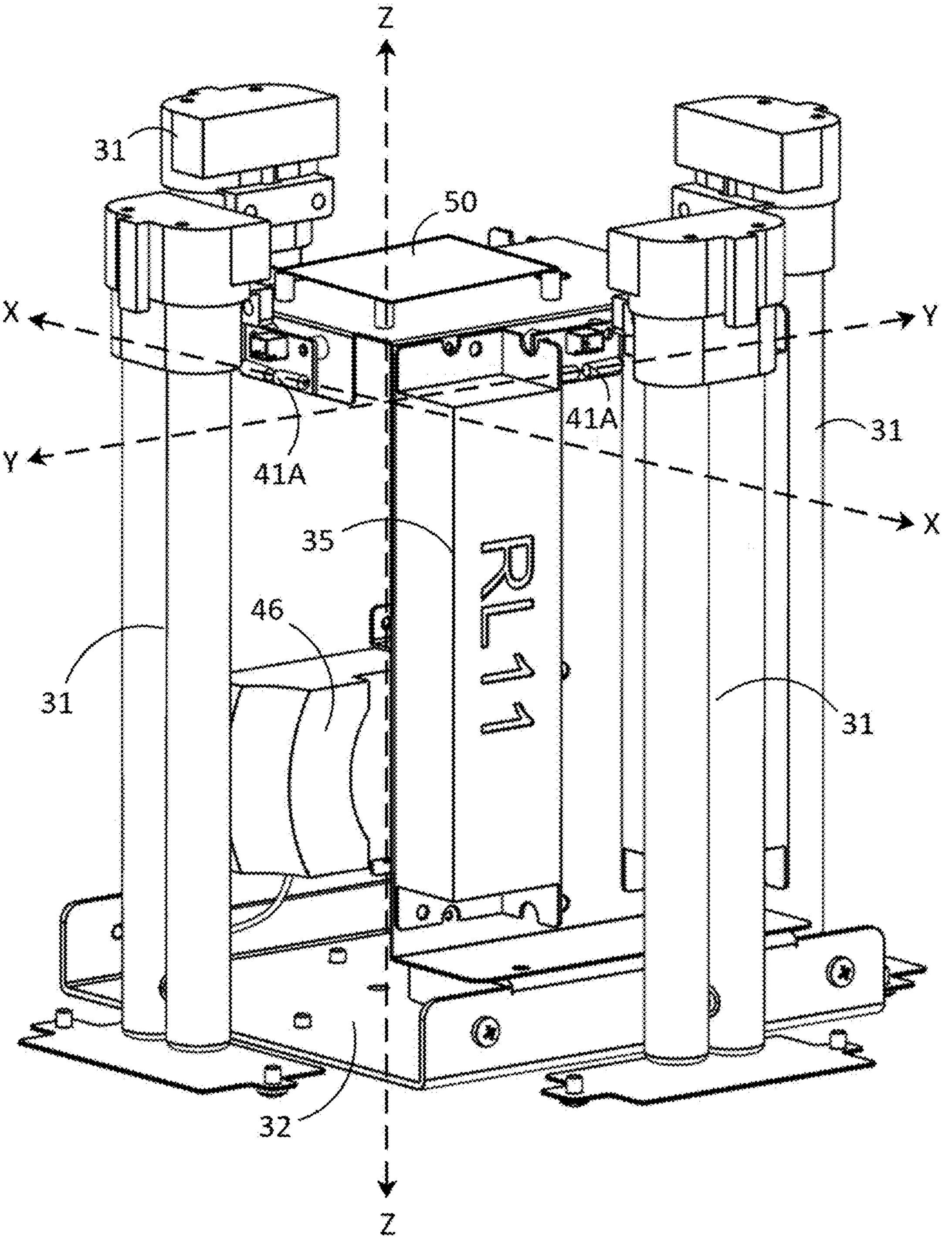
FIG. 6—shows a side perspective view showing some example components of an UV light emitting assembly according to various embodiments described herein.
Figure 7:
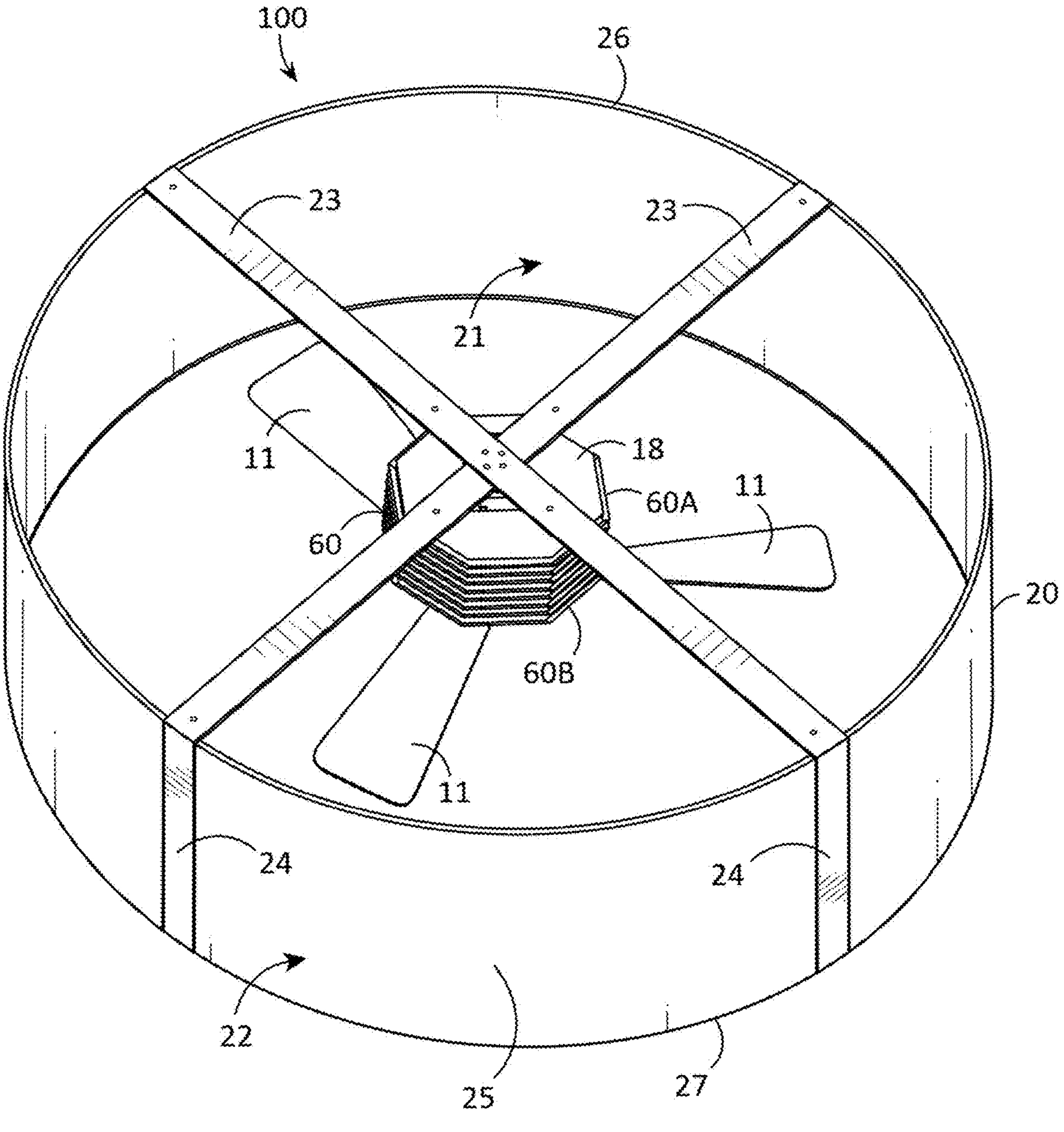
FIG. 7—depicts a top perspective view of a further example of an air moving sanitation device according to various embodiments described herein.

A UV light emitting assembly 30 may be configured in any shape and size. Referring to the example of FIG. 6, in some embodiments, a UV light emitting assembly 30 may comprise a lower assembly plate 32 and an upper assembly plate 33 that may be coupled together via one or more central assembly plates 34. The motor hub 12 may be coupled to the lower assembly plate 32 and one or more of a mounting plate 13, downrod 16, and support arms 17 may be coupled to the upper assembly plate 33. Optionally, four UV light emitting elements 31 may be coupled to the UV light emitting assembly 30. Preferably, the device 100 may comprise one or more central assembly walls which may be coupled to a UV light emitting element 31, lower assembly plate 32, and/or upper assembly plate 33, and the central assembly plates 34 may provide structural support. Central assembly plates 34 may be reflective to UV radiation 80 to direct UV radiation 80 away from the center of the UV light emitting assembly 30 and/or otherwise impermeable to UV radiation 80 to protect internal electronics of the UV light emitting assembly 30. An electronic ballast 35 may be coupled to the lower assembly plate 33, central assembly plate 34, or other element of a UV light emitting assembly 30, which may provide power to the UV light emitting elements 31. A ballast 35 is a type of electrical resistor or reactance, fixed in-line with the circuits that supply mains power to a light bulb. The core role of a lighting ballast 35 is to help control and regulate the supplied current during different operating phases (and voltages) for certain bulb types. In some embodiments, a remote control receiver 46 may be coupled to the central assembly plate 34. In some embodiments, a control unit 50 may be coupled to the upper assembly plate 33.

Preferably, the one or more UV light emitting elements 31 may provide Ultraviolet germicidal irradiation (UVGI). The term "ultraviolet (UV) light" should be understood to include any source of man-made UV light technology including lamps, LEDs, and types such as 2-pin, 4-pin, screw-in, T5 bi-pin, plug-in compact, etc. In preferred embodiments, a UV light emitting element 31 may emit UV radiation 80 that comprises or that is substantially Ultraviolet C (UVC) radiation with a wavelength of approximately 100-280 nanometers.

The device 100 may comprise one or more, such as a plurality of, baffle plates 60 which may direct or limit the UV radiation 80 emitted by the one or more UV light emitting elements 31 in a horizontal direction that is substantially parallel to the horizontal blade plane 71. Preferably, the one or more baffle plates 60 may direct or limit the UV radiation 80 emitted by the one or more UV light emitting elements 31 in a horizontal direction that is above the fan blades and that is below the mounting plate 13. In some embodiments, the device 100 may comprise two or more, such as all, baffle plates 60 that may be spaced apart (such that the lower plate surface 62 of an upper baffle plate 60 and the upper plate surface 63 of a lower baffle plate 60 that are adjacent to each other) at a minimum of between approximately 0.1 inches and 10.0 inches apart from each other.

In preferred embodiments, baffle plates 60 may be made from or may comprise a material that is resistant to UV-C light and/or may be coated with a material coating that may be resistant to UV-C light. In preferred embodiments, baffle plates 60 may be made from or may comprise a material that is anti-reflective to UV-C light wavelengths. Example materials and coatings that are resistant to UV-C light and that are anti-reflective to UV-C light wavelengths include: Black Zinc Oxide, Titanium Dioxide and other in-organic materials may be used in coatings on metal, fabric or plastic materials.

In preferred embodiments, the device 100 may comprise at least two baffle plates 60, such as a top baffle plate 60A and a bottom baffle plate 60B, that may be coupled to the UV light emitting assembly 30. The top baffle plate 60A may be coupled to the UV light emitting assembly 30 so that the top baffle plate 60A is relatively closer to the mounting plate 13 than the bottom baffle plate 60B. Optionally, one or more, such as a plurality of central baffle plates 60C may be coupled to the UV light emitting assembly 30 so that the one or more central baffle plates 60C may be positioned between the top baffle plate 60A and the bottom baffle plate 60B.

Baffle plates 60 may be configured in any shape and size. In preferred embodiments, a baffle plate 60 may be generally flat or planar in shape. In some embodiments, the device 100 may comprise two or more baffle plates 60 that may be generally flat or planar in shape and the two or more baffle plates 60 may be substantially parallel to each other (plus or minus 10 degrees, and more preferably plus or minus five degrees, and more preferably plus or minus less than one degree). In some embodiments, the baffle plates 60 may be spaced approximately between one and twenty centimeters apart so that the lower plate surface 62 and upper plate surface 63 of two adjacent baffle plates 60 may be spaced approximately between one and twenty centimeters apart. In further embodiments, the device 100 may comprise any number of baffle plates, having any spacing distance between plates. Optionally, the baffle plates 60 and/or their lower plate surfaces 62 and upper plate surfaces 63 may be angled relative to each other, such as being more than ten degrees from being parallel to each other.

In some embodiments, one or more baffle plates 60, such as one or more central baffle plates 60C, may encircle the UV light emitting assembly 30 so that the one or more baffle plates 60, such as one or more central baffle plates 60C, may encircle one or more, such as all, UV light emitting elements 31 that are coupled to the UV light emitting assembly 30. For example, a baffle plate 60 may comprise an aperture 61 through which a UV light emitting assembly 30 may be inserted or disposed.

Each baffle plate may comprise a lower plate surface 62 and an upper plate surface 63. Generally, a lower plate surface 62 may face away from the ceiling or other object that the device 100 is coupled to, such as to face a floor surface above which the device 100 is suspended, when the baffle plate 60 is coupled to the UV light emitting assembly 30. Generally, an upper plate surface 63 may face towards the ceiling or other object that the device 100 is coupled to, such as to face a ceiling surface below which the device 100 is suspended, when the baffle plate 60 is coupled to the UV light emitting assembly 30. In preferred embodiments, a baffle plate 60 may comprise a lower plate surface 62 and an upper plate surface 63 that may each be flat or planar in shape.

In preferred embodiments, the device 100 may comprise a top baffle plate 60A and bottom baffle plate 60B that may be coupled to the UV light emitting assembly 30 so that the one or more UV light emitting elements 31 that are coupled to UV light emitting assembly 30 are positioned between the top baffle plate 60A and the bottom baffle plate 60B so that the UV radiation 80 emitted by the one or more UV light emitting elements 31 does not contact the upper plate surface 63 of the top baffle plate 60A and so that the UV radiation 80 does not contact the lower plate surface 62 of the bottom baffle plate 60B.

Figure 3:
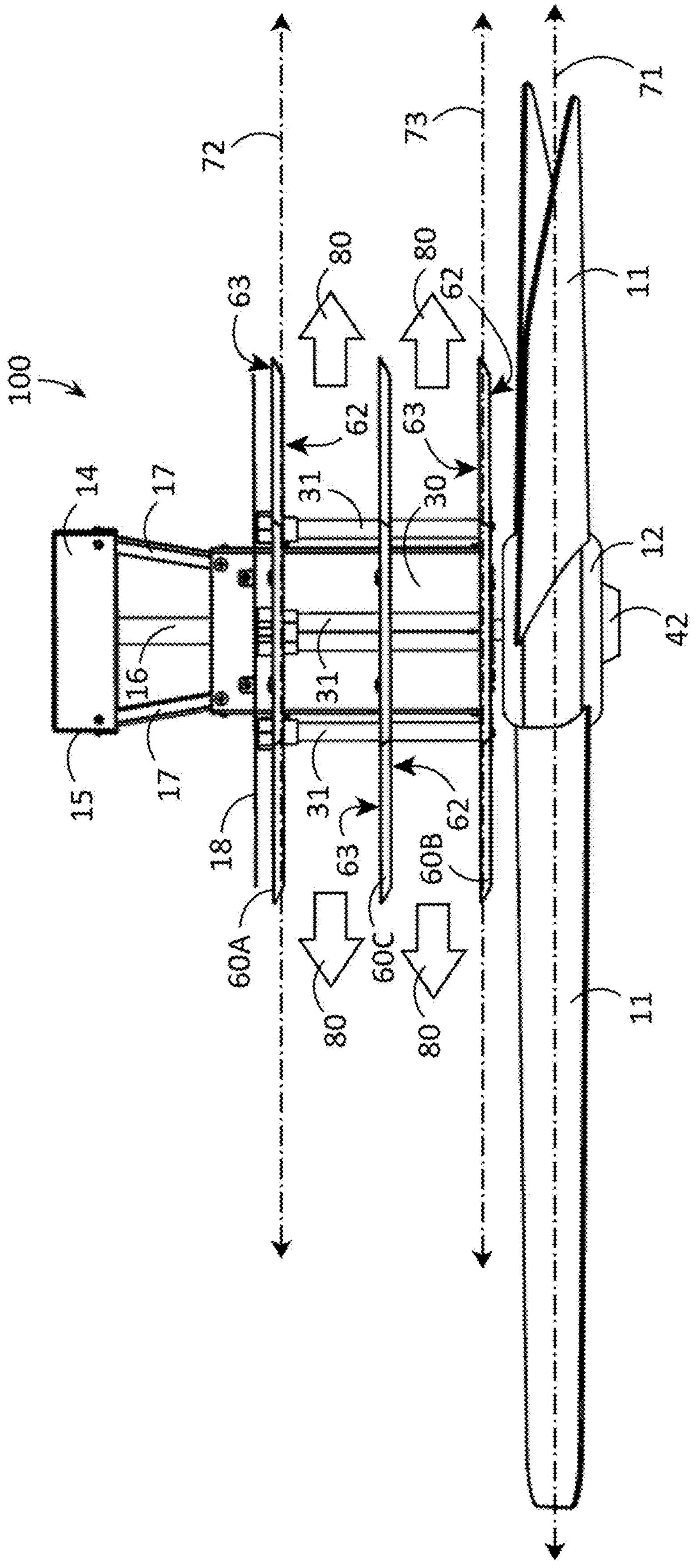
FIG. 3—shows a side elevation view of another example of an air moving sanitation device according to various embodiments described herein.
Figure 4:
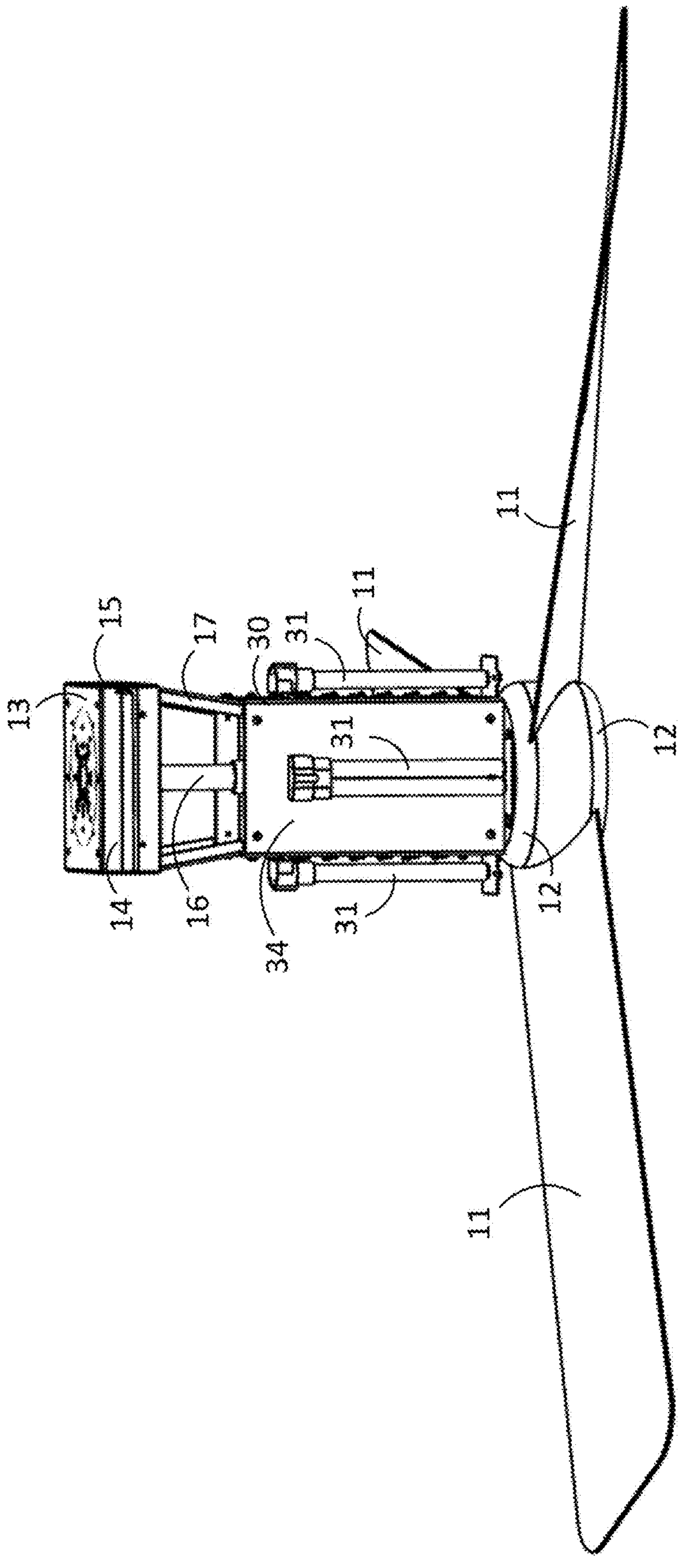
FIG. 4—depicts a side perspective view showing some example components of an air moving sanitation device according to various embodiments described herein.
Figure 5:
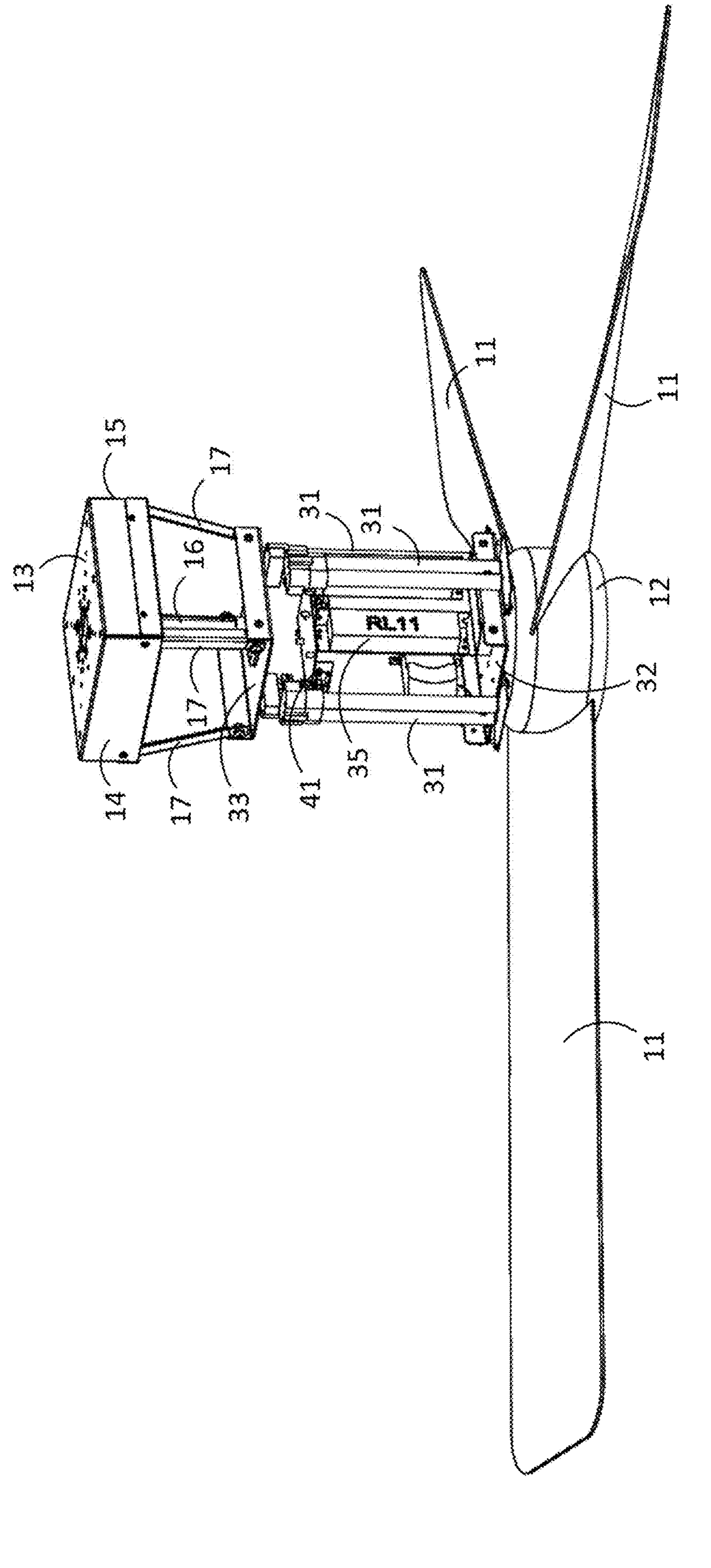
FIG. 5—illustrates a side perspective view showing some further example components of an air moving sanitation device according to various embodiments described herein.

In preferred embodiments, and as perhaps best shown in FIGS. 1 and 3, the device 100 may comprise a top baffle plate 60A and a bottom baffle plate 60B, that may be coupled to the UV light emitting assembly 30. The top baffle plate 60A may be coupled to the UV light emitting assembly 30 so that the top baffle plate 60A is relatively closer to the mounting plate 13 than the bottom baffle plate 60B. The top baffle plate 60A may comprise a lower plate surface 62 and the bottom baffle plate 60B may comprise an upper plate surface 63. The one or more UV light emitting elements 31 may be positioned below the lower plate surface 62 of the top baffle plate 60A so that the lower plate surface 62 may limit the UV radiation 80 emitted by the one or more UV light emitting elements 31 from exceeding above an upper horizontal UV light plane 72, the upper horizontal UV light plane 72 below the mounting plate 13, and the upper plate surface 63 of the bottom baffle plate 60B may limit the radiation emitted by the one or more UV light emitting elements 31 from exceeding below a lower horizontal UV light plane 73, the lower horizontal UV light plane 73 above the horizontal blade plane 71. In preferred embodiments, the upper horizontal UV light plane 72 and/or the lower horizontal UV light plane 73 may be substantially perpendicular (within two degrees of perpendicular) to the force or action of gravity, e.g., the horizontal blade plane 71 of the fan blades 11 is substantially perpendicular to the ground or horizontal surface above which the device 100 is suspended. In preferred embodiments, the upper horizontal UV light plane 72 and/or the lower horizontal UV light plane 73 may be substantially parallel (within five degrees of being parallel) to the horizontal blade plane 71.

The upper horizontal UV light plane 72 of the device 100 may be formed by the lower plate surface 62 of the top baffle plate 60A being made from or being coated with a material that is non-reflective to UVC radiation so that the lower plate surface 62 may limit the UV radiation 80 emitted by the one or more UV light emitting elements 31 from exceeding above the upper horizontal UV light plane 72. Likewise, the lower horizontal UV light plane 73 of the device 100 may be formed by the upper plate surface 63 of the bottom baffle plate 60B being made from or being coated with a material that is non-reflective to UVC radiation so that the upper plate surface 63 may limit the UV radiation 80 emitted by the one or more UV light emitting elements 31 from exceeding below the lower horizontal UV light plane 73. In preferred embodiments, substantially all (greater than 99%) of the UV radiation 80 emitted by the UV light emitting elements 31 of the device 100 is emitted between the lower plate surface 62 of the top baffle plate 60A and the upper plate surface 63 of the bottom baffle plate 60B so that substantially all (greater than 99%) of the UV radiation 80 emitted by the UV light emitting elements 31 of the device 100 is emitted between the upper horizontal UV light plane 72 and lower horizontal UV light plane 73. In preferred embodiments, the upper horizontal UV light plane 72 and the lower horizontal UV light plane 73 may be substantially parallel (plus or minus 10 degrees, and more preferably plus or minus five degrees, and more preferably plus or minus less than one degree) to the horizontal blade plane 71.

The lower horizontal UV light plane 73 may be above the horizontal blade plane 71 of the device 100 to prevent any direct viewing from occupants in the room within a set radius wherein the UV-C light can be harmful for eyes and skin. The upper horizontal UV light plane 72 is below the ceiling or other object that the device 100 may be suspended from and below the mounting plate 13 to prevent the UV radiation 80 from extending upwards and damaging materials on the ceiling like plastics which are commonly used as lighting diffusers and painted surfaces and to prevent the UV radiation 80 from extending upwards and contacting sprinkler heads, since many types of sprinkler head covers are made from chromed or reflective materials that can reflect UV radiation 80 back downwards into the room where occupants may be present.

In some embodiments, the device 100 may comprise a shroud 20 having a one or more shroud vertical walls 25 that surrounds the UV light emitting elements 31, and the one or more shroud vertical walls 25 may substantially block (block greater than 99%) of the UV radiation 80 emitted by the UV light emitting elements 31 from passing through the shroud 20. In preferred embodiments, a shroud 20 may surround the UV light emitting elements 31 to extend above the upper horizontal UV light plane 72 and to extend below the lower horizontal UV light plane 73 so that the shroud 20 substantially blocks the UV radiation 80 emitted by the UV light emitting elements 31 from passing through the shroud 20.

Figure 8:
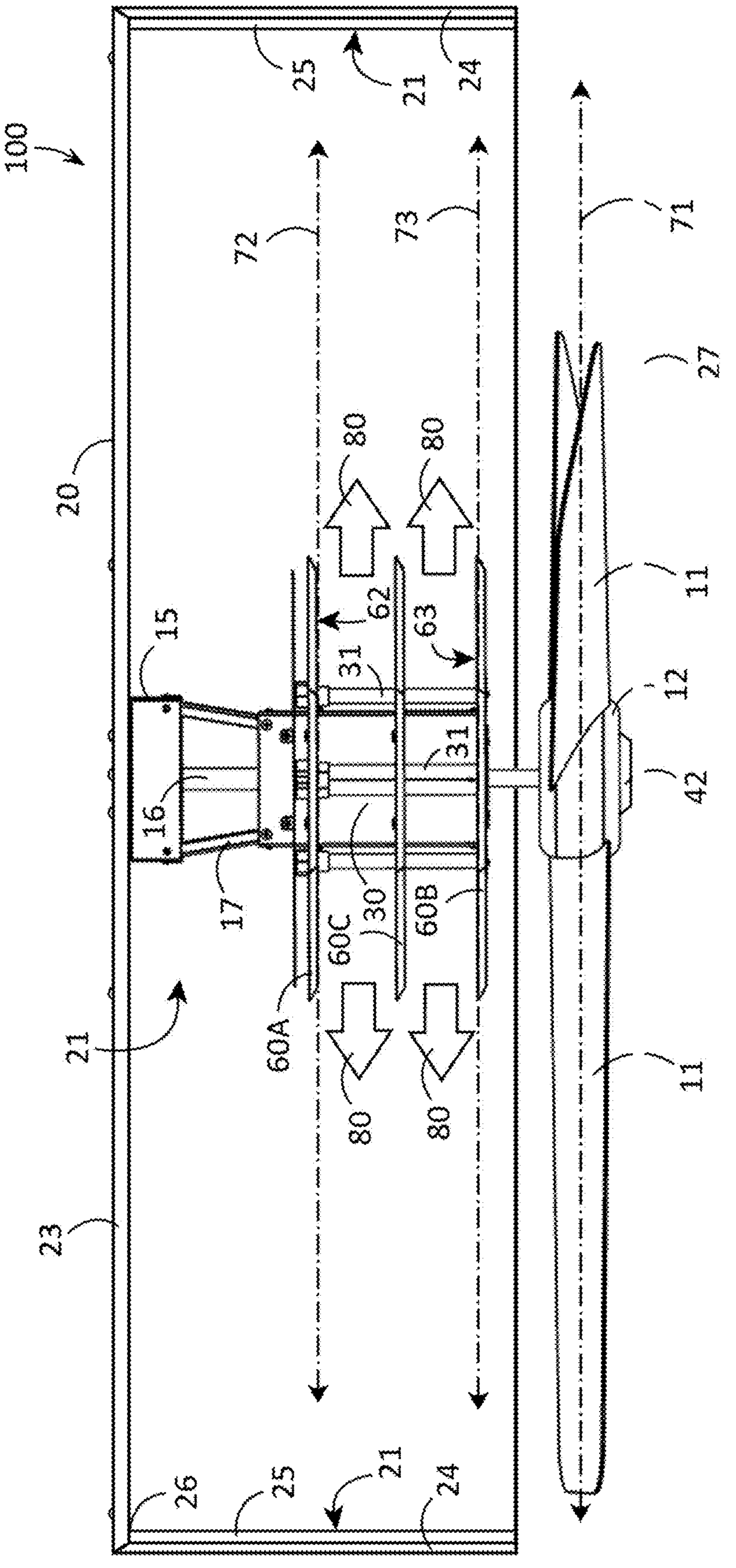
FIG. 8—illustrates a side elevation view of the example air moving sanitation device of FIG. 7 having a portion of its shroud removed according to various embodiments described herein.
Figure 9:
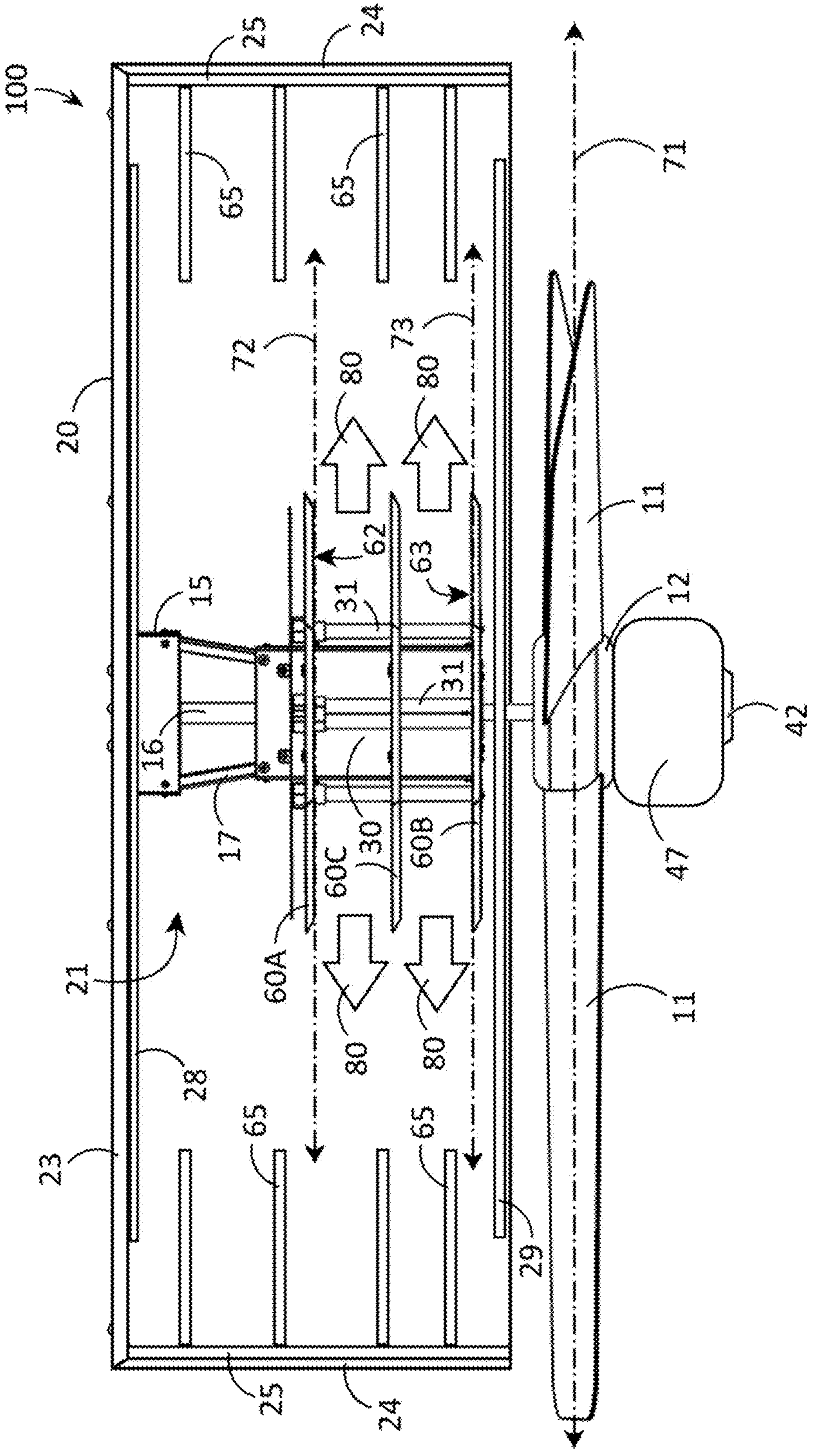
FIG. 9—illustrates a side elevation view of another example of an air moving sanitation device having a portion of its shroud removed according to various embodiments described herein.
Figure 10:
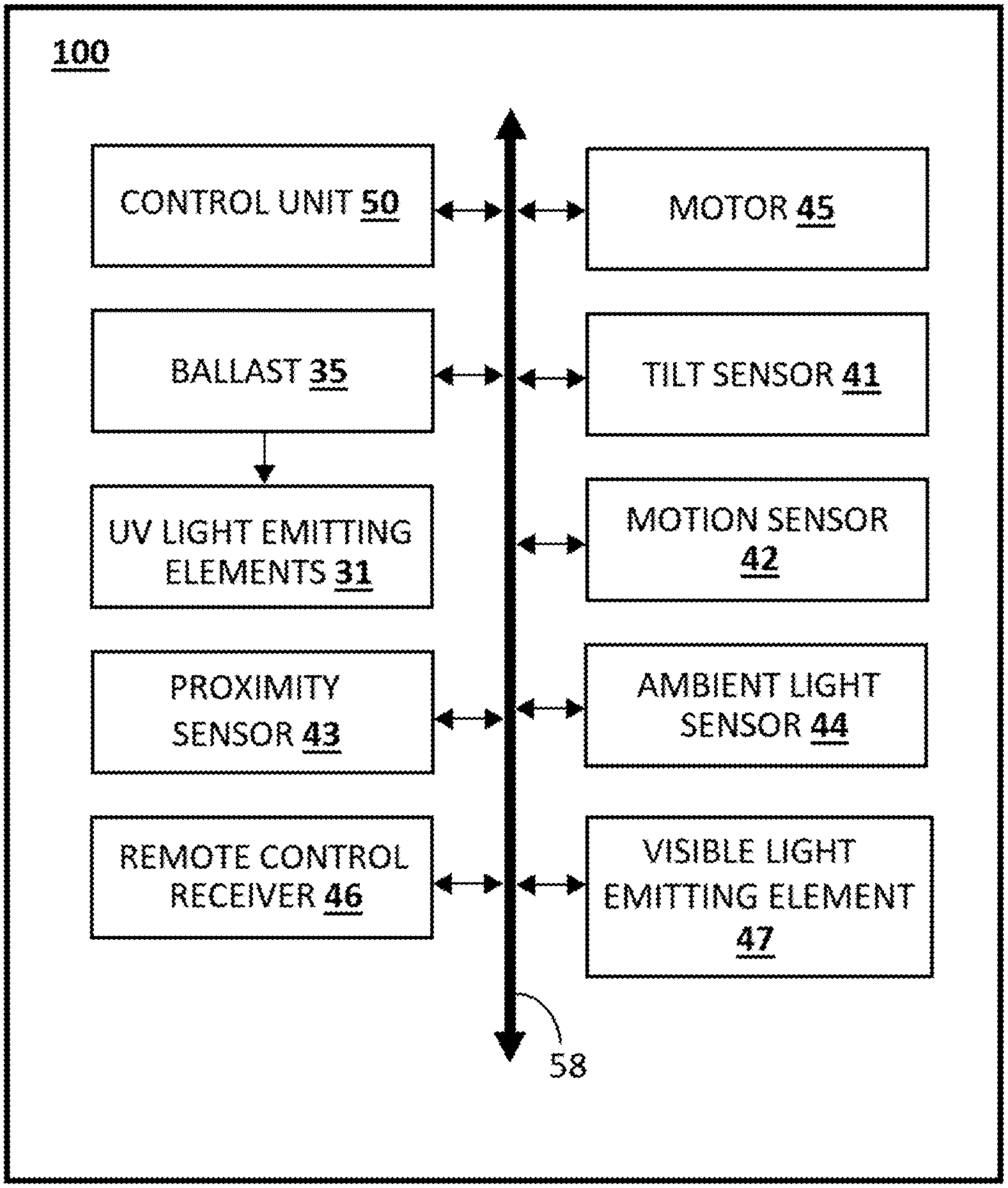
FIG. 10—shows a block diagram depicting some example components that an air moving sanitation device may include according to various embodiments described herein.

A shroud 20 may comprise one or more shroud vertical walls 25 that may be configured in any size and shape. In preferred embodiments, a shroud vertical wall 25 may be generally cylindrical in shape, octagonal in shape, or configured in any other shape including combinations of shapes, having an open shroud lower perimeter 27 and an open shroud upper perimeter 26 and may encircle the UV light emitting assembly 30. A shroud 20 may comprise a shroud lower perimeter 27 that may be larger than the diameter of the fan blades 11 (as shown in FIG. 8), may be approximately equal to the diameter of the fan blades 11, or that may be smaller than the diameter of the fan blades 11 (as shown in FIG. 9). A shroud 20 may comprise an interior surface 21 and an exterior surface 22. An interior surface 21 may face the UV light emitting assembly 30, and an exterior surface 22 may be positioned on the opposite side of the shroud 20 relative to the interior surface 21 so that the exterior surface 22 faces the environment around the device 100. Optionally, a shroud 20 may be generally cylindrical in shape and may encircle the UV light emitting assembly 30 and the fan blades 11 and optionally the motor hub 12. In other embodiments, a shroud 20 may comprise a rectangular or square prism shape having an open shroud lower perimeter 27 and an open shroud upper perimeter 26, a triangular prism shape having an open shroud lower perimeter 27 and an open shroud upper perimeter 26, or any other shape.

A shroud vertical wall 25 may be made from or may comprise a rigid or flexible material(s) that substantially blocks (blocks greater than 95%) of the UV radiation 80 emitted by the UV light emitting elements 31 from passing through the shroud vertical wall 25. In preferred embodiment, the shroud 20 may comprise a substantially rigid shroud vertical wall 25 that may be made from or may comprise a plastic material, aluminum or other metal, or any other substantially rigid material that may be treated with a UV resistant coating, such as may be applied to the interior surface 21 and/or exterior surface 22, that is anti-reflective for UV-C light. In preferred embodiment, the shroud 20 may comprise a flexible shroud vertical wall 25 that may be made from or may comprise a lightweight polyester fabric treated with a UV resistant coating, such as may be applied to the interior surface 21 and/or exterior surface 22, that is anti-reflective for UV-C light. Example materials and coatings that are resistant to UV-C light and that are anti-reflective to UV-C light wavelengths include: Black Zinc Oxide, Titanium Dioxide and other in-organic materials may be used in coatings on metal, fabric or plastic materials. A flexible shroud vertical wall 25 may comprise a resilient material, such as a wire or plastic filament disposed throughout the shroud upper perimeter 26 and/or shroud lower perimeter 27 which may be used to help the shroud 20 maintain or regain its shape, such as after being compressed or folded for shipping and packaging.

The shroud 20 and its components, such as lateral shroud supports 23, vertical shroud supports 24, and shroud vertical wall 25, may use materials or coatings with UV stabilizers, absorbers or blockers. Some Organic compounds such as benzophenones and benzotriazoles are typical absorbers which selectively absorb the UV and re-emit at a less harmful wavelength, mainly as heat.

The shroud 20 and its components, such as lateral shroud supports 23, vertical shroud supports 24, and shroud vertical wall 25, may use Fabrics, foam, plastics, metal housings or metal frame parts that may be treated with UV light absorber materials or blocker materials to prevent UV light from being emitted outside of the shroud 20.

In practice, the various types of additives may be used in combinations, or are compounded into the original materials to be produced as a special grade for UV protection for use in constructing the shroud 20.

In embodiments of the device 100 having a shroud 20, the device 100 may comprise two or more baffle plates 60. Optionally, a device 100 having a shroud 20 may have the same number of baffle plates 60 as a non-shrouded device 100 or fewer baffle plates 60 as a non-shrouded device 100 since the shroud 20 substantially blocks the UV radiation 80 (UV-C light) from going outward further into the room. A shroud 20 can be used in rooms where UV-C light should be blocked to protect occupants or materials in a room.

The air gap between the device 100 baffle plates 60 and the shroud 20 allows air to be pulled through the air gap(s) proximate to the shroud upper perimeter 26 and shroud lower perimeter 27 by the fan blades 11 that are external to the shroud 20 and the air is treated with UV-C radiation 80 as it passes through the air gap(s).

In some embodiments, the device 100 may comprise one or more lateral shroud supports 23 that may be coupled to the shroud 20 and/or to one or more vertical shroud supports 24. Lateral shroud supports 23 may support and position the shroud 20 to surround the UV light emitting elements 31 of the UV light emitting assembly 30 so that the shroud 20 extends above the upper horizontal UV light plane 72 and extends below the lower horizontal UV light plane 73 so that the shroud 20 substantially blocks the UV radiation 80 emitted by the UV light emitting elements 31 from passing through the shroud 20. A lateral shroud support 23 may comprise a length of, preferably substantially rigid material, that may be coupled to the mounting plate 13, vertical walls 14, UV light emitting assembly 30, or other element of the device 100.

In some embodiments, the device 100 may comprise one or more vertical shroud supports 24 that may be coupled to the shroud 20 and/or to a lateral shroud support 23, and which may support and position the shroud 20 to surround the UV light emitting elements 31 of the UV light emitting assembly 30 so that the shroud 20 extends above the upper horizontal UV light plane 72 and extends below the lower horizontal UV light plane 73 so that the shroud 20 substantially blocks the UV radiation 80 emitted by the UV light emitting elements 31 from passing through the shroud 20. A vertical shroud support 24 may comprise a length of, preferably substantially rigid material, that may be coupled to a lateral shroud support 23, to the interior surface 21 of the shroud 20, and/or to the exterior surface 22 of the shroud 20. Preferably, one or more vertical shroud supports 24 may be used to maintain the shape of a shroud 20 made of a flexible material while one or more lateral shroud supports 23 may be coupled to one or more vertical shroud supports 24 and/or to the shroud 20 to maintain the positioning of the shroud 20.

In some embodiments, and as shown in FIG. 9, a shroud 20 may comprise a shroud top wall 28 and/or a shroud bottom wall 29. A shroud top wall 28 may be configured in any size and shape. Generally, a shroud top wall 28 may be coupled to or proximate to the shroud upper perimeter 26 and may extend across a portion of the shroud upper perimeter 26 to physically block UV radiation 80 while still allowing air to enter (optionally exit depending on rotation direction of the fan blades 11) the shroud 20 so as to provide an air gap between the shroud top wall 28 and the interior surface 21 of the shroud vertical wall 25 that may let air pass into the shroud 20 for exposure to UV radiation in the shroud 20. A shroud bottom wall 29 may be configured in any size and shape. Generally, a shroud bottom wall 29 may be coupled to or proximate to the shroud lower perimeter 27 and may extend across a portion of the shroud lower perimeter 27 to physically block UV radiation 80 while still allowing air to exit (optionally enter depending on rotation direction of the fan blades 11) the shroud 20 so as to provide an air gap between the shroud bottom wall 29 and the interior surface 21 of the shroud vertical wall 25 that may let air pass out of the shroud 20 after exposure to UV radiation in the shroud 20. Preferably, a shroud top wall 28 and/or a shroud bottom wall 29 may be made from the same or similar UV light absorber materials or blocker materials to prevent UV light 80 from passing through the shroud 20 or being emitted into the environment outside of the shroud 20.

In some embodiments, and as shown in FIG. 9, a shroud 20 may comprise one or more shroud plates 65 which may be coupled to the shroud vertical wall 25 and which may extend away from the shroud vertical wall 25. Shroud plates 65 may be configured in any size and shape. In some embodiments, shroud plates 65 may be configured similar to baffle plates 60 so that the shroud plates 60 may direct or limit the UV radiation 80 emitted by the one or more UV light emitting elements 31 in a horizontal direction that is substantially parallel to the horizontal blade plane 71. Preferably, the one or more shroud plates 65 may direct or limit the UV radiation 80 emitted by the one or more UV light emitting elements 31 in a horizontal direction that is above the fan blades 11 and that is below the mounting plate 13. In preferred embodiments, shroud plates 65 may be made from or may comprise any material that may be used to form baffle plates 60, such as material that is resistant to UV-C light and/or may be coated with a material coating that may be resistant to UV-C light.

In some embodiments, the device 100 may comprise a shroud 20, lateral shroud supports 23, and vertical shroud supports 24 that may be lightweight and easy to install, such as by having a shroud vertical wall 25 comprising a polyester material with UV resistant coating that can be coiled up during shipping and released to open to full size when the device 100 is installed in a room.

In some embodiments, the device 100 may comprise a tilt sensor 41 that may be configured to detect the tilt or orientation of the device 100. A tilt sensor 41 is an instrument that is used for measuring the tilt in one or more axes of a reference plane. Tilt sensors 41 measure the tilting position of objects with reference to gravity and are used in numerous applications. They enable the easy detection of orientation or inclination. Tilt sensors 41 may include mercury switches, tilt switches or rolling ball sensors, a micro electro-mechanical system (MEMS) tilt sensor, any other type of device or sensor which may be used to detect an object being tilted in one or more directions. As an example, a tilt sensor 41 may have a tilt switch 41A that may include a metallic ball that is designed to move when the sensor reaches a predetermined angle, and the metallic ball may make electrical contact when the device 100 is tilted or not tilted to generate electrical communication to indicate tilt or to interrupt electrical communication in response to tilt, e.g., to deactivate motion of the fan blades 11 and/or to deactivate UV light emitting elements 31. In preferred embodiments, the device may comprise a tilt sensor 41 that may have one or more tilt switches 41A that may be coupled to a UV light emitting assembly 30. For example and referring to FIG. 6, the device 100 may comprise a first tilt switch 41A that may detect tilt in the x-axis (shown by line X-X) and a second tilt switch 41A that may detect tilt in the y-axis (shown by line Y-Y) as tilt in the x-axis or y-axis would result in the device 100 being tilted out of the z-axis (shown by line Z-Z) and therefore result in the device 100 being tilted out of vertical.

In some embodiments, the device 100 may comprise a tilt sensor 41 that is configured to detect when the device 100 has been tilted out of vertical. In preferred embodiments, the device 100 may be vertical when the horizontal blade plane 71 of the fan blades 11 is substantially perpendicular (within two degrees of perpendicular) to the force or action of gravity, e.g., the horizontal blade plane 71 of the fan blades 11 is substantially perpendicular to the ground or horizontal surface above which the device 100 is suspended. The tilt sensor 41 may detect when the device 100 is tilted out of vertical to exceed a tilt threshold.

In some embodiments, the tilt threshold may be defined by the horizontal blade plane 71 being more than plus or minus ten degrees from vertical. In some embodiments, the tilt threshold may be defined by the horizontal blade plane 71 being more than five degrees from vertical. In some embodiments, the tilt threshold may be defined by the upper horizontal UV light plane 72 and/or the lower horizontal UV light plane 73 being more than ten degrees from vertical. In some embodiments, the tilt threshold may be defined by the upper horizontal UV light plane 72 and/or the lower horizontal UV light plane 73 being more than five degrees from vertical.

In preferred embodiments, the motion of the fan blades 11 and/or the UV light emitting element(s) 31 may be deactivated once the tilt sensor 41 detects that the tilt of the device 100 out of vertical exceeds the tilt threshold. In some embodiments, the tilt sensor 41 is configured to deactivate the motion of the fan blades 11 and the UV light emitting element(s) 31 once the tilt sensor 41 detects that the tilt of the device 100 out of vertical exceeds the tilt threshold. In some embodiments, a control unit 50 is configured to deactivate the motion of the fan blades 11 and the UV light emitting element(s) 31 once the tilt sensor 41 detects that the tilt of the device 100 out of vertical exceeds the tilt threshold.

In some embodiments, the device 100 may comprise a motion sensor 42 that may be configured to detect motion proximate to the device 100. A motion sensor 42 may be coupled to any element of the device 100. In some embodiments, a motion sensor 42 may be coupled to a visible light emitting element 47 (FIG. 9) so that the motion sensor 42 faces the floor or other surface below the device 100. In preferred embodiments, a motion sensor 42 may be coupled to the motor hub 11 (FIG. 8), and more preferably coupled to the bottom of the motor hub 12 so that the motion sensor 42 faces the floor or other surface below the device 100. Example motion sensors 42 include: passive infrared motion sensors, microwave motion sensors, ultrasonic motion sensors, tomographic motion sensors, video camera software, or any other type of sensor configured to detect motion in an area. In some embodiments, the device 100 may comprise a motion sensor 42 and the device 100 may be configured to deactivate the motion of the fan blades 11 and/or to deactivate the UV light emitting elements 31 once the motion sensor 42 detects motion that is proximate to the motion sensor 42. In some embodiments, the device 100 may comprise a motion sensor 42 and the device 100 may be configured to activate (e.g., starts rotating) the motion of the fan blades 11 and/or to activate (e.g., starts emitting UV radiation 80) the UV light emitting elements 31 once the motion sensor 42 detects motion that is proximate to the motion sensor 42. Motion proximate to the motion sensor 42 may comprise motion being detected within 100 feet of the motion sensor 42, more preferably within 50 feet of the motion sensor 42, and more preferably within 20 feet of the motion sensor 42.

In some embodiments, the device 100 may comprise a proximity sensor 43. In preferred embodiments, the motion of the fan blades 11 and/or the UV light emitting element(s) 31 may be deactivated once the proximity sensor 43 detects that an object has entered a proximity threshold of the device 100. In some embodiments, the proximity sensor 43 is configured to deactivate the motion of the fan blades 11 and the UV light emitting element(s) 31 once the tilt sensor 41 detects that an object has entered a proximity threshold of the device 100. In some embodiments, a control unit 50 is configured to deactivate the motion of the fan blades 11 and the UV light emitting element(s) 31 once the proximity sensor 43 detects that an object has entered a proximity threshold of the device 100. In some embodiments, the tilt threshold may be defined by an object entering within 100 feet of the proximity sensor 43, more preferably within 50 feet of the proximity sensor 43, and more preferably within 20 feet of the proximity sensor 43.

A proximity sensor 43 may comprise any type of sensor which is able to provide information which describes the distance between the proximity sensor 43 and an object or surface that the proximity sensor 43 is directed towards. Proximity sensors 43 may include sensors such as fixed (single beam) or rotating (sweeping) Time-of-Flight (TOF) or structured light based laser rangefinders, 3D High Definition LiDAR, 3D Flash LIDAR, 2D or 3D sonar sensors and one or more 2D cameras. Further, a proximity sensor 43 may also include Passive thermal infrared sensors, Photocell or reflective sensors, photoelectric, or 'eye-beam' sensors, Radar sensors, Reflection of ionizing radiation sensors, Sonar sensors, such as active or passive, Ultrasonic sensors, Fiber optics sensors, Hall effect sensors, or any other sensor able to detect the presence of nearby objects and surfaces without any physical contact.

In some embodiments, the motion sensor 42 may activate the device 100 when motion is detected in the room that the device 100 is installed in to start the air sanitization function when people are present. For example, once a motion sensor 42 detects motion proximate to the device 100 or in the room that the device 100 is installed in, the motion of the fan blades 11 may be activated and/or the one or more UV light emitting elements 31 may be activated to generate UV radiation 80.

In some embodiments, the device 100 may comprise an ambient light sensor 44 which may be configured to detect ambient light levels in the environment that the device 100 is positioned in. In preferred embodiments, the motion of the fan blades 11 and/or the UV light emitting element(s) 31 may be deactivated once an ambient light sensor 44 detects that the ambient light level of the environment that the device 100 is positioned in has exceeded an ambient light threshold of the device 100. In preferred embodiments, the motion of the fan blades 11 and/or the UV light emitting element(s) 31 may be activated once an ambient light sensor 44 detects that the ambient light level of the environment that the device 100 is positioned in has fallen below an ambient light threshold of the device 100. In some embodiments, the ambient light sensor 44 is configured to deactivate and/or activate the motion of the fan blades 11 and the UV light emitting element(s) 31 once the ambient light sensor 44 detects that the ambient light level of the environment that the device 100 is positioned in has exceeded or fallen below an ambient light threshold of the device 100. In some embodiments, a control unit 50 is configured to deactivate and/or activate the motion of the fan blades 11 and the UV light emitting element(s) 31 once the ambient light sensor 44 detects that the ambient light level of the environment that the device 100 is positioned in has exceeded or fallen below an ambient light threshold of the device 100. In some embodiments, the ambient light threshold may be defined by 100 to 300 lux, more preferably 500 to 800 lux, and more preferably 800 to 1,700 lux.

In preferred embodiments, an ambient light sensor 44 may be or comprise a passive device that converts the light energy into an electrical signal output. Ambient light sensors 44 are more commonly known as Photoelectric Devices or Photo Sensors because they convert light energy (photons) into electronic signals (electrons). An ambient light sensor 44 may detect light levels via any suitable detection mechanism including: Photoemission or photoelectric effect; thermal; polarization; photochemical; and weak interaction effects. Example ambient light sensors 44 include: Active-pixel sensors (APSs), Cadmium zinc telluride radiation detectors, Charge-coupled devices (CCD), HgCdTe infrared detectors, LEDs which are reverse-biased to act as photodiodes, Photoresistors or Light Dependent Resistors (LDR), Photodiodes which can operate in photovoltaic mode or photoconductive mode, Phototransistors, which act like amplifying photodiodes, Quantum dot photoconductors or photodiodes, and Photovoltaic cells or solar cells.

In some embodiments, the device 100 may comprise a remote control receiver 46 which may enable a user to operate the functions of the device 100 remotely. In preferred embodiments, a remote control receiver 46 may enable a user to operate the functions of the device 100 in a wireless manner, such as by operating via an infrared, Wi-Fi, Radio Frequency (RF), Bluetooth, or other wireless electronic communication protocol. In further embodiments, a remote control receiver 46 may enable a user to operate the functions of the device 100 using a wired electronic connection.

In some embodiments, the device 100 may comprise a visible light emitting element 47 that is configured to illuminate an environment external to the shroud 20, such as below the fan blades 11 when the device 100 is coupled to a ceiling or other structure that is above a floor surface. In preferred embodiments, a visible light emitting element 47 may generate light between 400 and 700 nanometers (nm) in wavelength, such as that is commonly used in indoor environments. A visible light emitting element 47 may comprise any suitable visible light emitting device, such as a light-emitting diode (LED), incandescent light bulb, fluorescent light bulb, halogen light bulb, high-intensity discharge light bulb, electroluminescent light source, neon light source, or any other type of suitable light source. In further embodiments, a visible light emitting element 47 may comprise standard size two feet by two feet, two feet by four feet, etc., LED Flat panel light fixtures, Troffer light fixtures, and other light fixtures. A Troffer light fixture is a rectangular light fixture that fits into a modular dropped ceiling grid (i.e. two feet by two feet or two feet by four feet). Troffer fixtures typically accommodate standard fluorescent lamps (T12, T8, or T5), integral LED sources, and other light sources.

In some embodiments, the device 100 may comprise a control unit 50 which may be in electronic communication with two or more of the motor 45, UV light emitting elements 31, tilt sensor 41, motion sensor 42, proximity sensor 43, ambient light sensor 44, remote control receiver 46, and/or visible light emitting element 47.

In some embodiments, a control unit 50 may enable electronic communication between the motor 45, UV light emitting elements 31, tilt sensor 41, motion sensor 42, proximity sensor 43, ambient light sensor 44 and/or remote control receiver 46 so that one or more of the tilt sensor 41, motion sensor 42, proximity sensor 43, ambient light sensor 44, visible light emitting element 47, and/or remote control receiver 46 may be able to activate and/or deactivate the motor 45 (and therefore activate and/or deactivate motion of the fan blades 11), the UV light emitting elements 31, and/or visible light emitting element 47. For example, a control unit 50 may comprise a circuit board or other wired electronic interface.

Figure 11:
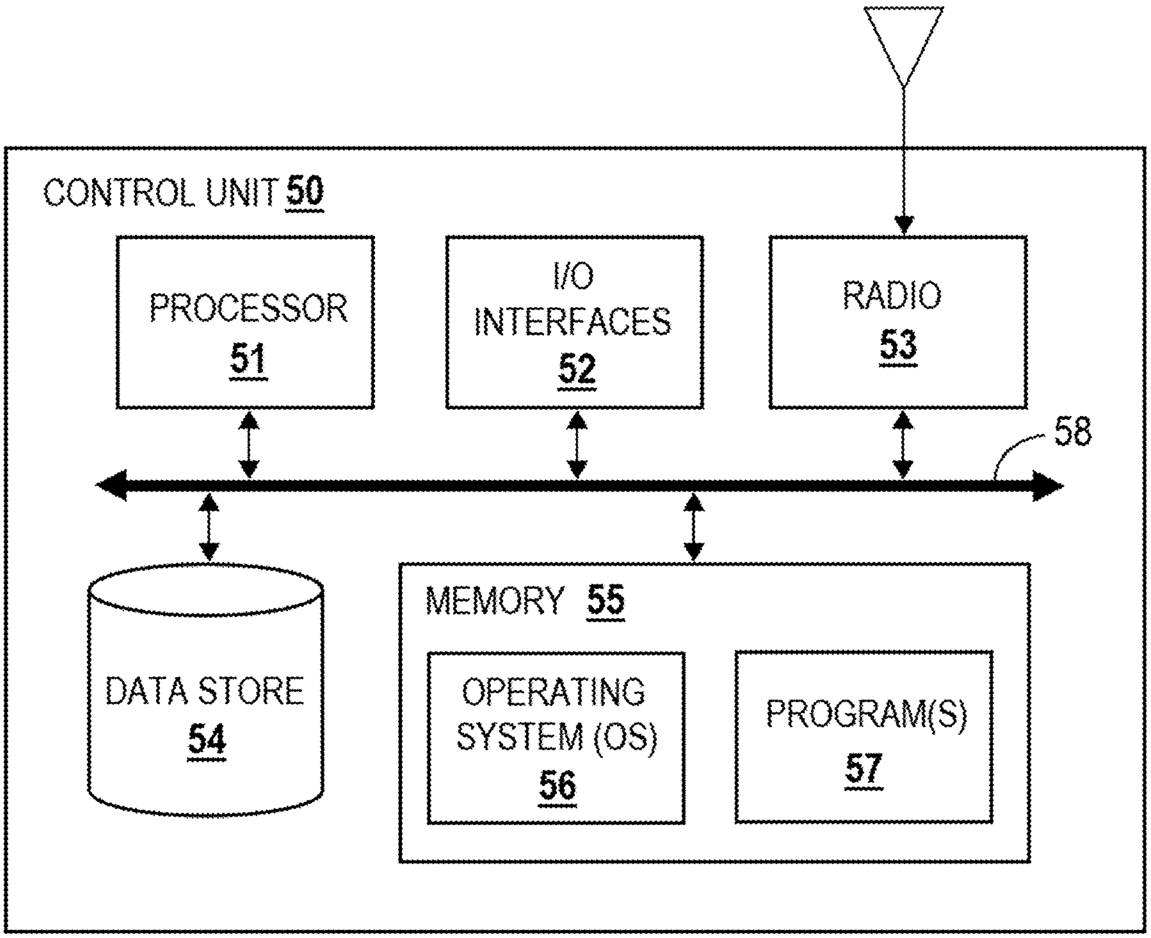
FIG. 11—depicts a block diagram illustrating an example of a control unit according to various embodiments described herein.

In some embodiments, a control unit 50 may be in electronic communication with the motor 45, UV light emitting elements 31, tilt sensor 41, motion sensor 42, proximity sensor 43, ambient light sensor 44 and/or remote control receiver 46 so that the control unit 50 may be able to activate and/or deactivate (and control the speed of) the motor 45 (and therefore activate and/or deactivate motion of the fan blades 11), visible light emitting element 47, and/or the UV light emitting elements 31 based on information communicated to the control unit 50 from a tilt sensor 41, motion sensor 42, proximity sensor 43, ambient light sensor 44 and/or remote control receiver 46. As an example, the device 100 can be a digital device that, in terms of hardware architecture, comprises a control unit 50 which may include one or more of a processor 51, input/output (I/O) interfaces 52, a radio module 53, a data store 54, and memory 55. It should be appreciated by those of ordinary skill in the art that FIG. 11 depicts the control unit 50 in an oversimplified manner, and a practical embodiment may include additional components or elements and suitably configured processing logic to support known or conventional operating features that are not described in detail herein.

The control unit 50 and electronic elements (30, 31, 41, 42, 43, 44, 45, 46, 47) may be communicatively coupled via a local interface 58. The local interface 58 can be, for example but not limited to, one or more buses, circuit boards, wiring harnesses, or other wired connections or wireless connections, as is known in the art. The local interface 58 can have additional elements, which are omitted for simplicity, such as controllers, buffers (caches), drivers, repeaters, and receivers, among many others, to enable communications. Further, the local interface 58 may include address, control, and/or data connections to enable appropriate communications among the aforementioned components.

A processor 51 is a hardware device for executing software instructions. A processor 51 can be any custom made or commercially available processor, a central processing unit (CPU), an auxiliary processor among several processors associated with the control unit 50, a semiconductor-based microprocessor (in the form of a microchip or chip set), or generally any device for executing software instructions. When the control unit 50 is in operation, the processor 51 is configured to execute software stored within the memory 55, to communicate data to and from the memory 55, and to generally control operations of the device 100 pursuant to the software instructions and/or from instructions received from a remote control and/or other electronic elements (30, 31, 41, 42, 43, 44, 45, 46, 47). In an exemplary embodiment, the processor 51 may include a mobile optimized processor, such as optimized for power consumption and mobile applications.

The I/O interfaces 52 can be used by a user to provide user input and display system output data, such as operational status, from the device 100. The I/O interfaces 52 can include, for example, buttons, knobs, switches, LED indicator lights, LED display, LCD display, a serial port, a parallel port, a small computer system interface (SCSI), an infrared (IR) interface, a radio frequency (RF) interface, a universal serial bus (USB) interface, and the like. In some embodiments, I/O interfaces 52 may comprise buttons, knobs, switches, etc., that may be manipulated by a user 201 to enable the user to select one or more settings for the motor 45 and UV light emitting elements 31.

A radio 53 may enable wireless communication to an external access device or network. In preferred embodiments, a radio 53 may operate via Wi-Fi communication standards. Any number of suitable wireless data communication protocols, techniques, or methodologies can be supported by the radio 53, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Near-Field Communication (NFC); Frequency Hopping Spread Spectrum; Long Term Evolution (LTE); cellular/wireless/cordless telecommunication protocols (e.g. 3G/4G/5G, etc.); wireless home network communication protocols; paging network protocols; magnetic induction; satellite data communication protocols; wireless hospital or health care facility network protocols such as those operating in the WMTS bands; GPRS; proprietary wireless data communication protocols such as variants of Wireless USB; and any other protocols for wireless communication.

An optional data store 54 may be used to store data. The data store 54 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 54 may incorporate electronic, magnetic, optical, and/or other types of storage media.

The memory 55 may include any of volatile memory elements (e.g., random access memory (RAM, such as DRAM, SRAM, SDRAM, etc.)), nonvolatile memory elements (e.g., ROM, hard drive, etc.), and combinations thereof. Moreover, the memory 55 may incorporate electronic, magnetic, optical, and/or other types of storage media. Note that the memory 55 may have a distributed architecture, where various components are situated remotely from one another, but can be accessed by the processor 51. The software in memory 55 can include one or more software programs, each of which includes an ordered listing of executable instructions for implementing logical functions. In the example of FIG. 11, the software in the memory system 55 optionally includes a suitable operating system (O/S) 56 and program(s) 57. The operating system 56 essentially controls the execution of input/output interface 52 and other element functions, and provides scheduling, input-output control, file and data management, memory management, and communication control and related services. The operating system 56 may be, for example, LINUX (or another UNIX variant), Android (available from Google), Symbian OS, Microsoft Windows CE, Microsoft Windows 7 Mobile, iOS (available from Apple, Inc.), webOS (available from Hewlett Packard), Blackberry OS (Available from Research in Motion), and the like. The programs 57 may include various applications, add-ons, etc. configured to provide end user functionality of the device 100. In a typical example, one or more of the programs 57 may comprise instructions for controlling the functions of the motor 45 and UV light emitting elements 31.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequence of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

The control unit 50 may also include a main memory, such as a random access memory (RAM) or other dynamic storage device (e.g., dynamic RAM (DRAM), static RAM (SRAM), and synchronous DRAM (SDRAM)), coupled to the bus for storing information and instructions to be executed by the processor 51. In addition, the main memory may be used for storing temporary variables or other intermediate information during the execution of instructions by the processor 51. The control unit 50 may further include a read only memory (ROM) or other static storage device (e.g., programmable ROM (PROM), erasable PROM (EPROM), and electrically erasable PROM (EEPROM)) coupled to the bus for storing static information and instructions for the processor 51.

While some exemplary shapes and sizes have been provided for elements of the device 100, it should be understood to one of ordinary skill in the art that the fan blades 11, UV light emitting assembly 30, mounting plate 13, optional shroud 20, and any other element described herein may be configured in a plurality of sizes and shapes including "T" shaped, "X" shaped, square shaped, rectangular shaped, cylinder shaped, cuboid shaped, hexagonal prism shaped, triangular prism shaped, or any other geometric or non-geometric shape, including combinations of shapes. It is not intended herein to mention all the possible alternatives, equivalent forms or ramifications of the invention. It is understood that the terms and proposed shapes used herein are merely descriptive, rather than limiting, and that various changes, such as to size and shape, may be made without departing from the spirit or scope of the invention.

Additionally, while some materials have been provided, in other embodiments, the elements that comprise the device 100 may be made from or may comprise durable materials such as aluminum alloys, steel, aluminum, other metals and metal alloys, wood, hard rubbers, hard plastics, fiber reinforced plastics, carbon fiber, fiberglass, resins, polymers or any other suitable materials including combinations of materials. Additionally, one or more elements may be made from or may comprise durable and slightly flexible materials such as soft plastics, silicone, soft rubbers, or any other suitable materials including combinations of materials. In some embodiments, one or more of the elements that comprise the device 100 may be coupled or connected together with heat bonding, chemical bonding, adhesives, clasp type fasteners, clip type fasteners, rivet type fasteners, threaded type fasteners, other types of fasteners, or any other suitable joining method. In other embodiments, one or more of the elements that comprise the device 100 may be coupled or removably connected by being press fit or snap fit together, by one or more fasteners such as hook and loop type or Velcro® fasteners, magnetic type fasteners, threaded type fasteners, sealable tongue and groove fasteners, snap fasteners, clip type fasteners, clasp type fasteners, ratchet type fasteners, a push-to-lock type connection method, a turn-to-lock type connection method, a slide-to-lock type connection method or any other suitable temporary connection method as one reasonably skilled in the art could envision to serve the same function. In further embodiments, one or more of the elements that comprise the device 100 may be coupled by being one of connected to and integrally formed with another element of the device 100.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. An air moving sanitation device, the device comprising:

a plurality of fan blades coupled to a motor hub, the plurality of fan blades configured to rotate in a horizontal blade plane;

a mounting plate;

an ultraviolet (UV) light emitting assembly coupled to the mounting plate and to the motor hub, the UV light emitting assembly positioned between the motor hub and the mounting plate, and the UV light emitting assembly having a UV light emitting element that is configured to emit UV radiation when activated and to stop emitting UV radiation when deactivated;

a top baffle plate and a bottom baffle plate coupled to the UV light emitting assembly, wherein the top baffle plate is coupled to the UV light emitting assembly so that the top baffle plate is relatively closer to the mounting plate than the bottom baffle plate, wherein the top baffle plate comprises a lower plate surface and the bottom baffle plate comprises an upper plate surface, wherein the lower plate surface limits the UV radiation emitted by the UV light emitting element from exceeding above an upper horizontal UV light plane, the upper horizontal UV light plane below the mounting plate, and wherein the upper plate surface limits the UV radiation emitted by the UV light emitting element from exceeding below a lower horizontal UV light plane, the lower horizontal UV light plane above the horizontal blade plane; and a tilt sensor that is configured to detect a tilt of the device out of vertical, wherein one of, rotation of the fan blades and the UV light emitting element, is deactivated once the tilt sensor detects that the tilt of the device out of vertical exceeds a tilt threshold.

2. The device of claim 1, wherein the motion of the fan blades and the UV light emitting element are deactivated once the tilt sensor detects that the tilt of the device out of vertical exceeds the tilt threshold.

3. The device of claim 1, wherein the tilt threshold is defined by the horizontal blade plane being more than ten degrees from vertical.

4. The device of claim 1, further comprising a motion sensor, wherein rotation of the fan blades is activated or deactivated once the motion sensor detects motion that is proximate to the motion sensor, and wherein the UV light emitting element is activated or deactivated once the motion sensor detects motion that is proximate to the motion sensor.

5. The device of claim 4, wherein the motion sensor is coupled to the motor hub.

6. The device of claim 1, further comprising a motion sensor and a visible light emitting element, wherein the motion sensor is coupled to one of the motor hub and the visible light emitting element.

7. The device of claim 1, wherein the motor hub does not rotate with the plurality of fan blades.

8. The device of claim 1, further comprising one or more central baffle plates, wherein the one or more central baffle plates encircle the UV light emitting assembly.

9. The device of claim 1, wherein substantially all of the UV radiation emitted by the UV light emitting element is emitted between the lower plate surface and the upper plate surface.

10. The device of claim 1, wherein the upper horizontal UV light plane and the lower horizontal UV light plane are substantially parallel to the horizontal blade plane.

11. An air moving sanitation device, the device comprising:

a plurality of fan blades coupled to a motor hub, the plurality of fan blades configured to rotate in a horizontal blade plane;

a mounting plate;

an ultraviolet (UV) light emitting assembly coupled to the mounting plate and to the motor hub, the UV light emitting assembly positioned between the motor hub and the mounting plate, and the UV light emitting assembly having a UV light emitting element that is configured to emit UV radiation when activated and to stop emitting UV radiation when deactivated;

a top baffle plate and a bottom baffle plate coupled to the UV light emitting assembly, wherein the top baffle plate is coupled to the UV light emitting assembly so that the top baffle plate is relatively closer to the mounting plate than the bottom baffle plate, wherein the top baffle plate comprises a lower plate surface and the bottom baffle plate comprises an upper plate surface, wherein the lower plate surface limits the UV radiation emitted by the UV light emitting element from exceeding above an upper horizontal UV light plane, the upper horizontal UV light plane below the mounting plate, and wherein the upper plate surface limits the UV radiation emitted by the UV light emitting element from exceeding below a lower horizontal UV light plane, the lower horizontal UV light plane above the horizontal blade plane;

a shroud that surrounds the UV light emitting element, wherein the shroud extends above the upper horizontal UV light plane, wherein the shroud extends below the lower horizontal UV light plane, wherein the shroud does not extend into the horizontal blade plane so that the fan blades are external to the shroud, wherein air is sanitized by being exposed to UV radiation emitted by the UV light emitting element as it passes between the UV Light emitting element and the shroud, and wherein the shroud substantially blocks the UV radiation emitted by the UV light emitting element from passing through the shroud or into an environment outside of the shroud.

12. The device of claim 11, further comprising a tilt sensor that is configured to detect a tilt of the device out of vertical, wherein the motion of the fan blades is deactivated and the UV light emitting element is deactivated once the tilt sensor detects that the tilt of the device out of vertical exceeds a tilt threshold.

13. The device of claim 11, further comprising a motion sensor, wherein rotation of the fan blades is configured to activate or deactivate once the motion sensor detects motion that is proximate to the motion sensor.

14. The device of claim 11, further comprising a motion sensor, wherein the UV light emitting element is configured to activate or deactivate once the motion sensor detects motion that is proximate to the motion sensor.

15. The device of claim 11, further comprising a motion sensor, wherein the UV light emitting element is configured to be one of, activated and deactivated, once the motion sensor detects motion that is proximate to the motion sensor, and wherein rotation of the fan blades is configured to be one of, activated and deactivated, once the motion sensor detects motion that is proximate to the motion sensor.

16. The device of claim 11, further comprising a motion sensor and a visible light emitting element, wherein the motion sensor is coupled to one of the motor hub and the visible light emitting element.

17. The device of claim 11, further comprising one or more central baffle plates, wherein the one or more central baffle plates encircle the UV light emitting assembly.

18. The device of claim 11, wherein substantially all of the UV radiation emitted by the UV light emitting element is emitted between the lower plate surface and the upper plate surface.

19. The device of claim 11, wherein the upper horizontal UV light plane and the lower horizontal UV light plane are substantially parallel to the horizontal blade plane.

20. The device of claim 11, further comprising a visible light emitting element, wherein the visible light emitting element is coupled to the motor hub.

* * * * *